(12) United States Patent
Charalambides et al.

(10) Patent No.: US 11,944,411 B2
(45) Date of Patent: Apr. 2, 2024

(54) WEARABLE DEVICE WITH MECHANICAL SPRING TO DETECT PULSE TRANSIT TIME

(71) Applicant: Lifeware Labs, LLC, Pittsburgh, PA (US)

(72) Inventors: Alexandros Charalambides, Pittsburgh, PA (US); Brian Stancil, Pittsburgh, PA (US)

(73) Assignee: Lifeware Labs, LLC, Pittsburgh, PA (US)

( * ) Notice: Subject to any disclaimer, the term of this patent is extended or adjusted under 35 U.S.C. 154(b) by 327 days.

(21) Appl. No.: 16/698,574

(22) Filed: Nov. 27, 2019

(65) Prior Publication Data

US 2020/0178817 A1     Jun. 11, 2020

Related U.S. Application Data

(60) Provisional application No. 62/883,721, filed on Aug. 7, 2019, provisional application No. 62/773,857, filed on Nov. 30, 2018.

(51) Int. Cl.
| | | |
|---|---|---|
| *A61B 5/0205* | (2006.01) | |
| *A61B 5/00* | (2006.01) | |
| *A61B 5/021* | (2006.01) | |
| *A61B 5/0245* | (2006.01) | |
| *A61B 5/1455* | (2006.01) | |
| *A61B 5/274* | (2021.01) | |
| *A61B 5/28* | (2021.01) | |
| *A61B 5/352* | (2021.01) | |

(52) U.S. Cl.
CPC ........ *A61B 5/02125* (2013.01); *A61B 5/0245* (2013.01); *A61B 5/14552* (2013.01); *A61B 5/274* (2021.01); *A61B 5/28* (2021.01); *A61B 5/352* (2021.01); *A61B 5/6823* (2013.01); *A61B 2560/0412* (2013.01); *A61B 2562/06* (2013.01); *A61B 2562/146* (2013.01); *A61B 2562/166* (2013.01)

(58) Field of Classification Search
CPC ... A61B 5/14551; A61B 5/0205; A61B 5/024; A61B 5/02438; A61B 5/02416
See application file for complete search history.

(56) References Cited

U.S. PATENT DOCUMENTS

2003/0208248 A1* 11/2003 Carter .................. A61N 1/0504
                                                            607/69

FOREIGN PATENT DOCUMENTS

CA          2305069 A1 * 10/2001   ........... B81B 3/0024
WO    WO-2014197822 A2 * 12/2014   ........... A61B 5/0024

* cited by examiner

*Primary Examiner* — Michael J D'Abreu
(74) *Attorney, Agent, or Firm* — Michael G. Monyok

(57) ABSTRACT

A wearable electronic device comprises a base for mounting a plurality of sensors, where the sensors acquiring physiological data of a user wearing the device. By providing multiple sensors on a single device, additional physiological data, such as pulse transit time, can be provided. To ensure quality data is collected, the device includes a spring mechanism for applying a compressive force on the sensor to force it into the skin of a user.

14 Claims, 6 Drawing Sheets

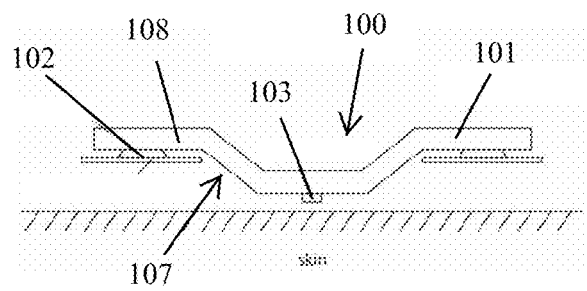 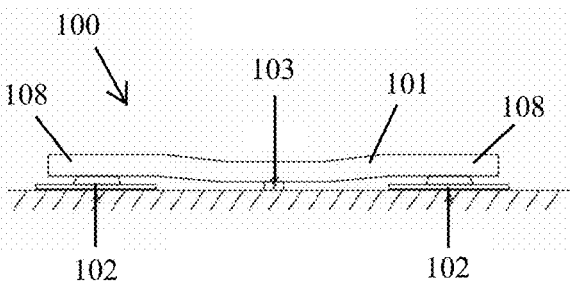
FIG. 1A　　　　　　　FIG. 1B
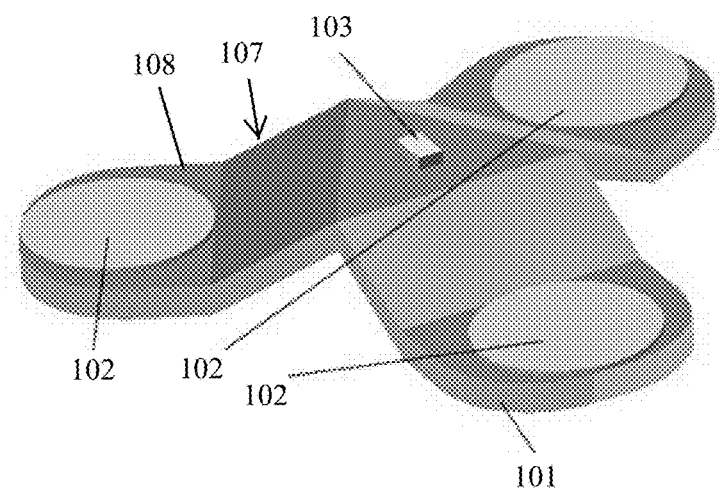
FIG. 2

WEARABLE DEVICE WITH MECHANICAL SPRING TO DETECT PULSE TRANSIT TIME

CROSS-REFERENCE TO RELATED APPLICATIONS

This application claims the benefit under 35 U.S.C. § 119 of Provisional Application Ser. No. 62/773,857, filed Nov. 30, 2018, and Provisional Application Ser. No. 62/883,721, filed Aug. 7, 2019, each of which is incorporated herein by reference.

STATEMENT REGARDING FEDERALLY SPONSORED RESEARCH

This invention was made with government support under W81XWH-18-C-0049 awarded by U.S. Army Medical Research Acquisition Activity. The government has certain rights in the invention.

BACKGROUND OF THE INVENTION

The invention relates to a wearable device capable of detecting, recording, and transmitting physiological data, such as pulse transit time. More specifically, the invention relates to a device that incorporates a blood pulse oximeter, including a mechanical spring to improve the quality of the data provided by the blood pulse oximeter, and other sensors to provide a multitude of physiological data from a single wearable device.

When a patient visits a hospital or doctor's office, a series of health measurements can be taken that may include a finger pulse oximeter reading (photoplethysmogram/PPG), blood pressure cuff measurement (BP), and an electrocardiogram (ECG or EKG). These measurements are important in assessing the current health state of an individual to facilitate proper care and treatment.

With the advent of modern electronics, there has been a push to miniaturize health monitoring equipment in effort to improve portability and increase the amount of prophylactic care. One important device that has been difficult to miniaturize is the standard blood pressure cuff. The blood pressure cuff uses an inflatable sleeve that typically envelopes the upper arm or wrist and is used to measure the arterial fluid pressure, or blood pressure, of an individual. Blood pressure is a strong indicator of cardiovascular health and is important because cardiovascular disease is the leading cause of death world-wide. Because the measurement relies on the cuff surrounding a patient's arm, miniaturization is difficult unless an alternative measurement protocol is used.

A possible alternative to the blood pressure cuff is to measure pulse transit time (PTT), sometimes referred to as pulse arrival time (PAT) and related to pulse wave velocity (PWV). PTT is the time it takes a pressure wave to travel from the heart, or a point near the heart, to some other point downstream in the blood. The speed that this pressure wave travels is dependent on blood pressure. For example, as blood pressure increases, the speed of the pulse wave also increases, and pulse transit time decreases. Therefore, as blood pressure increases, PTT decreases, and vice versa.

However, one challenge is that this approach requires two separate sources of measurement: one "upstream" measurement and one "downstream" measurement, where the time delay between detected heart beats at the upstream and downstream measurement is PTT (typically on the order of 10s-100s of milliseconds). In prior systems, this approach required two devices positioned at two locations, such as a pulse oximeter at the upper arm and a second pulse oximeter at the finger. Recent advancements have enabled PTT to be measured via one table-top device. This approach uses EKG to detect the instantaneous electrical heartbeat (the upstream measurement) and PPG to optically measure the pulsatile flow that arrives at the fingers (the downstream measurement). Using a device according to this approach, a person places a finger from each hand onto separate electrodes of the device, and then a finger over a co-located pulse oximeter. While improving upon the two-device system previously used, this approach is still not fully mobile and occupies both hands of the user.

Another challenge is that even if both EKG and PPG are co-located on a small and mobile device, it can be difficult to design a device that can simultaneously measure high quality EKG and PPG data due to the different requirements of each measurement. EKG requires two points of body contact that span across the heart muscle, while PPG requires an intimate contact with the body. Because PPG devices require good skin contact for an accurate measurement, PPG is typically measured via a clip-style device that is secured onto a user's finger, or on a wristwatch that can be tightly secured to a user's wrist via the wristband. Meanwhile, EKG cannot be measured using a finger or wrist alone. In some systems, a watch can be used to measure EKG by creating a first point of contact at the wrist and a second point of contact on the opposing hand, which must be brought into contact to the watch. However, since a voluntary movement is required to create the second contact point, this approach does not enable a continuous EKG reading and preoccupies both hands while measuring. In the cases where the user is sleeping, has limited mobility, or is missing a limb, this approach is not possible.

It would therefore be advantageous to develop monitoring equipment that would enable more continuous monitoring, increase an individual's freedom and mobility during monitoring, and reduce the amount of doctor visits related to routine testing. In addition, highly mobile health monitoring equipment could be applied to a wide range of applications, including military personnel who are located far away from health care facilities, as well as civilians interested in sports and general health monitoring.

BRIEF SUMMARY

According to embodiments of the present invention is a device, or patch, that can be worn by a user for continuous monitoring of EKG and PPG data without intervention from the user. In one embodiment, the patch comprises a base that provides contact points for EKG electrodes, pulse oximeter sensors, and adhesive for attachment to the user. A printed circuit board is attached to the base and provides an electrical connection to the various components of the patch.

This patch can be worn on the chest or back, and is capable of EKG, pulse oximetry, and accelerometry data measurements and can transmit the data in real-time. By combining the EKG and PPG signals, a measure for PTT can be extracted and therefore BP can be estimated. EKG is facilitated by commercially available off-the-shelf disposable Ag/AgCl electrodes that strongly adhere to the human skin. However, pulse oximetry is an optical-based measurement and therefore requires a highly intimate contact between the sensor and the user's skin for high quality data. Unlike prior devices, contact mechanisms such as finger clips and wrist straps are not available with an apparatus positioned on the chest. Rather, the device of the present invention achieves highly intimate contact through the use of a mechanical spring mechanism that can strongly press the pulse oximeter into the body, while maintaining a slim, low-profile shape. PTT can be calculated by identifying heartbeat peaks in the high quality EKG and PPG data.

BRIEF SUMMARY OF THE SEVERAL VIEWS OF THE DRAWINGS

FIGS. 1A and 1B are profile views of the device, according to one embodiment.

FIG. 2 is the device according to an alternative embodiment.

DETAILED DESCRIPTION

Figure 3A:
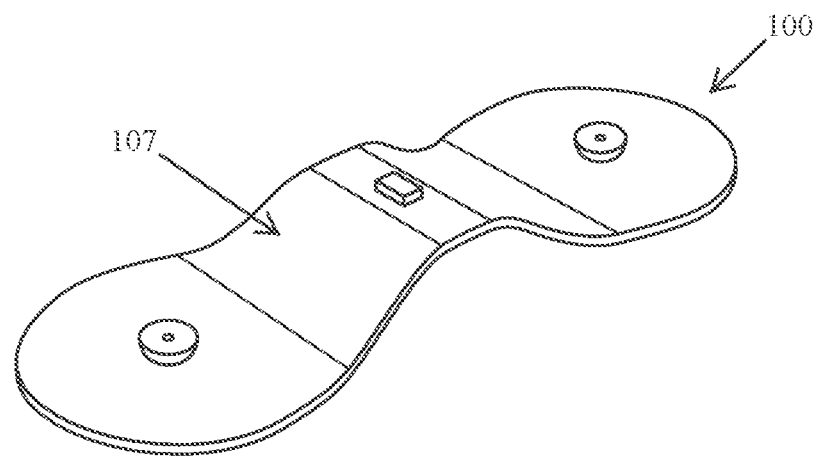
FIGS. 3A-3D show the spring mechanism of the device, according to several alternative embodiments.
Figure 3B:
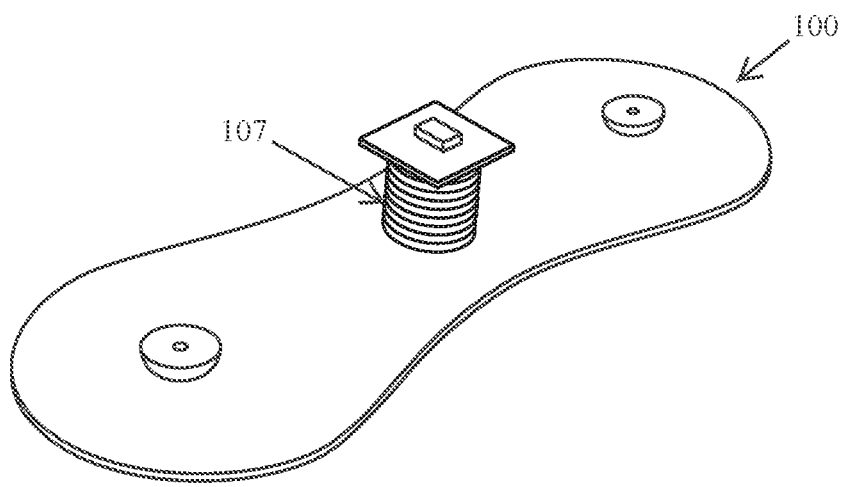
Figure 3C:
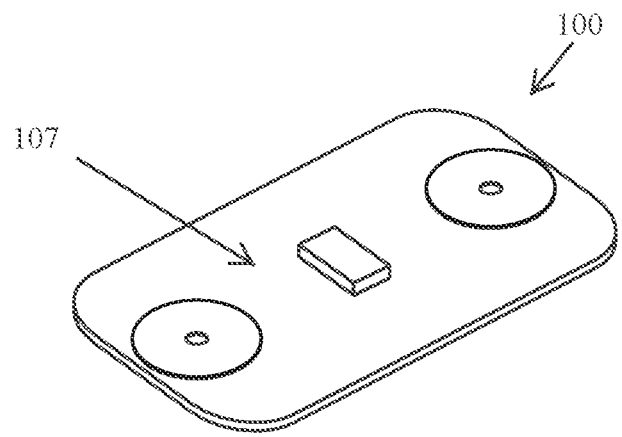
Figure 3D:
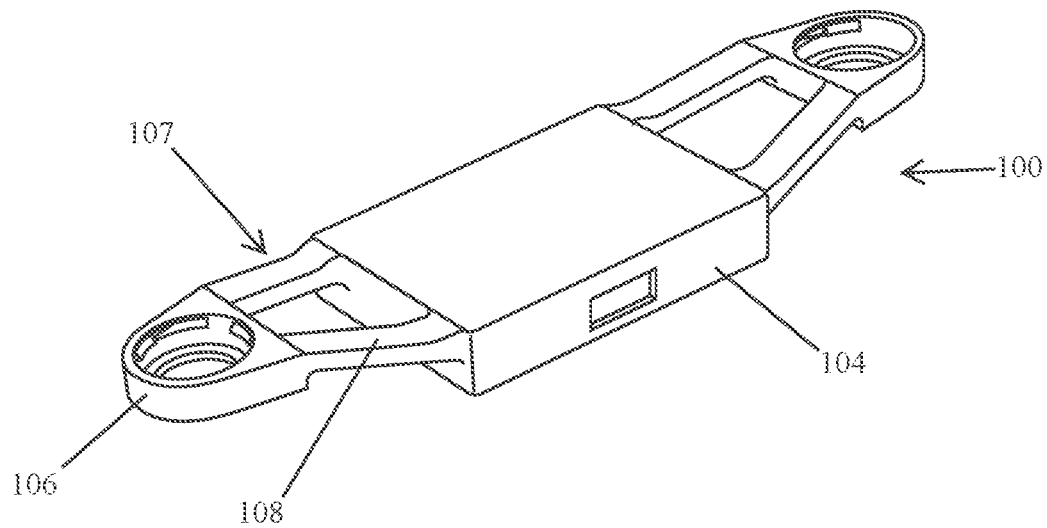

The patch 100, according to one example embodiment, can be seen in FIGS. 1A-1B. In FIG. 1A, the patch 100 is shown prior to attachment to the skin of a user. As shown in FIG. 1A, the patch 100 comprises a base 101 preformed in a curved, or stepped, configuration. More specifically, the profile view of the patch 100 in FIG. 1A shows the base 101 having a flat center portion that rises towards each end, forming a non-planar shape. In the embodiment shown in FIG. 1A, a biopotential electrode 102 is affixed to the bottom of each end and a pulse oximeter 103 is attached to the bottom of the center portion. The biopotential electrodes 102 have an adhesive that is used to attach the patch 100 to the skin of a user.

FIG. 1B depicts the patch 100 affixed to the skin of a user. As compared to the shape of the patch 100 in FIG. 1A, the shape of the patch 100 in FIG. 1B is flattened, with the electrodes 102 and pulse oximeter 103 all in contact with the skin of the user. To enable deformation from the unattached state, the base 101 comprises a flexible material, such as ABS plastic, creating a cantilever, or spring mechanism 107, between the biopotential electrodes 102 and pulse oximeter 103. Referring again to FIG. 1B, the ends of the base 101, or cantilevered arms 108, are depressed compared to the un-affixed shape of the base 101 depicted in FIG. 1A. In this configuration, the pulse oximeter 103, which is geometrically positioned closer to the body than the electrodes 102, is pressed into the skin of the user as the patch 100 deforms elastically. This elastic deformation creates a compressive force at the pulse oximeter 103. In addition to ABS plastic and other flexible polymers, the base 101 may comprise any material with a moderate Young's modulus and high yield strain. For example, a typical ABS plastic has a Young's Modulus of approximately 1 GPa and a yield strain of around 20%. Materials like these offer a compromise between the necessary stiffness required to exert sufficient force into the skin of a user, while also being bendable and accommodating to the curved surfaces typically seen on the chest and back. A person having skill in the art will appreciate that the shape and form of the base 101 can be manufactured according to various techniques, such as injection molding, 3D printing, milling, or any other general additive/subtractive manufacturing process.

The mechanical spring mechanism 107 can be employed in a variety of configurations. For example, FIG. 2 shows an alternative embodiment of the patch 100 with three electrodes 102 positioned around the center portion of the patch 100. In this embodiment, each electrode 102 is positioned on the same plane, which is different compared to the plane of the center portion of the patch 100 containing the pulse oximeter 103. While all three electrodes 102 occupy the same plane in this embodiment, a compressive force on the center portion of the patch 100 can be created with less than all electrodes 102 raised above the center portion.

FIGS. 3A-3D shows various configurations of the spring mechanism 107, which can take the form of a beam, spring, or other elastically deformable solid. For example, the apparatus can use a spring mechanism in the form of a curved cantilever beam (FIG. 3A), a helical-type spring (FIG. 3B), a straight cantilever beam (FIG. 3C), or a configuration (FIG. 3D) where the base 101 comprises a central housing 104 with protruding cantilever arms 108 extending from the central housing, where the arms 108 contain the electrode buckle snaps 106. In the embodiment depicted in FIG. 3D, wires extend from the central housing 104 through the cantilever arms 108, which are hollow, to electrically interface with the electrodes buckle snaps 106. In this embodiment, the majority of deformation occurs at the protruding cantilever arms 108 extending away from the central housing 104. The amount of deformation depends on the type of material used and its thickness or cross-section. In one example embodiment, the cantilever arms 108 are made from ABS plastic and have a thickness between 2-3 mm with a 1 mm hollow cross-section. In this configuration, the patch 100 is flexible enough to be applied to curved surfaces, yet stiff enough to transmit enough force onto the pulse oximeter 103.

Figure 4:
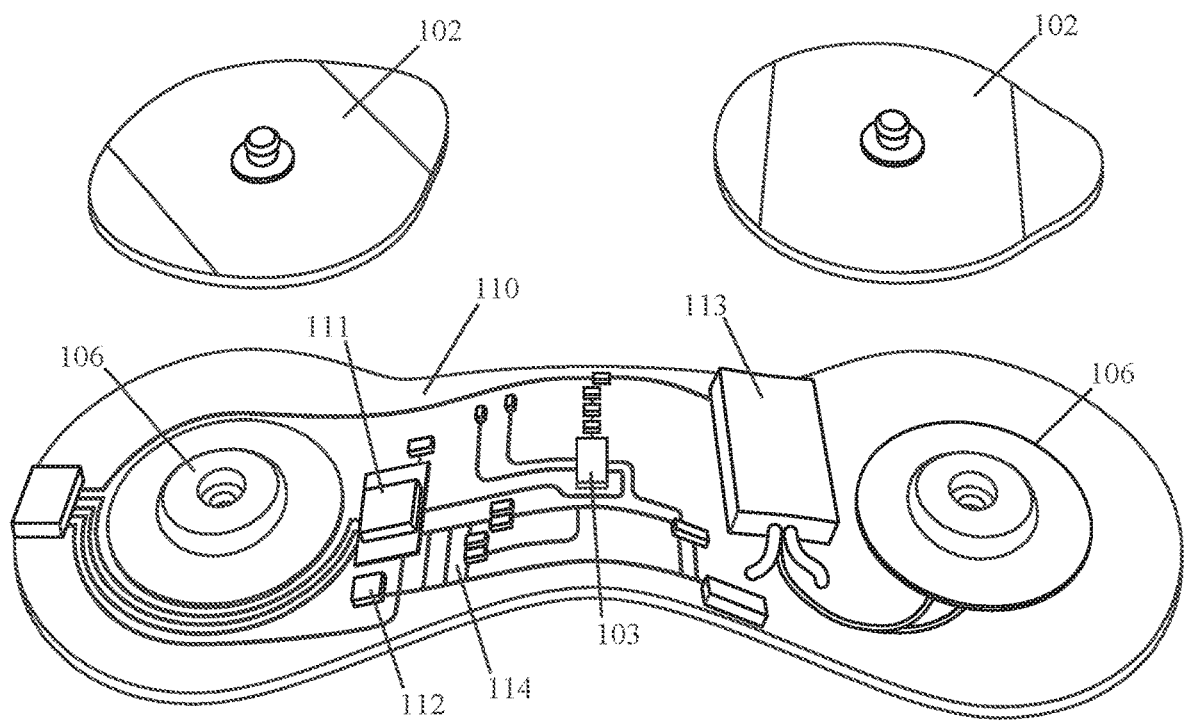
FIG. 4 shows various components of the device.

In addition to the base 101, electrodes 102, and pulse oximeter 103, the patch 100 further comprises various electronic components that permits the patch 100 to acquire, store, and transmit physiological data. FIG. 4 shows components contained within the interior of the patch 100 and includes a printed circuit board (PCB) 110 that electrically connects a microprocessor 111, an optional accelerometer 112, and a battery 113. The PCB 110 also connects the electrodes 102 (with or without buckle snaps 106), pulse oximeter 103, or other sensors disposed on the exterior of the patch 100. In one embodiment, the PCB 110 comprises a flexible PCB and is adhered to the base 101. In embodiments where the accelerometer 112 is used, the data acquired by the accelerometer 112 can be used to: (1) detect heart rate through undulations in the z-acceleration component; (2) filter noise due to motion artifacts in other sensor signals, such as the EKG and PPG signals; and (3) classify the current state or activity of the user, such as 'standing', 'running', or 'sleeping'. Depending on the state detected, the patch 100 can employ a specific sensor mode.

Figure 5:
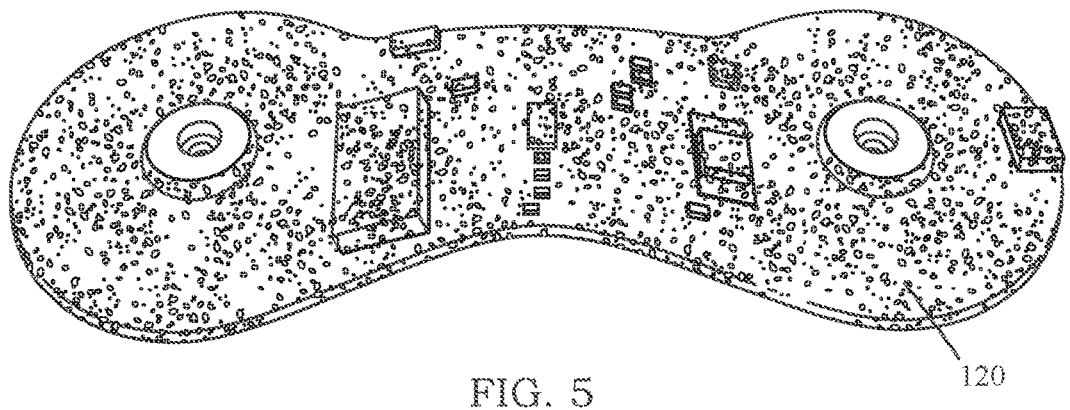
FIG. 5 shows the device with a protective cover, according to one embodiment.

The PCB 110 contains many of the components necessary to collect and wirelessly transmit physiological data. For example, the microprocessor 111 may include a Bluetooth radio that can be used to transmit data collected by the patch to an external device, such as a computer, tablet, or phone. In the embodiment shown in FIG. 4, an EKG filter 114 is connected to the microprocessor 111 and is used to filter acquired data prior to transmission. Other electrical components can be included depended on the intended application. To protect the electrical components of the patch 100, an insulating conformal coating 120 can be applied to the patch, as shown in FIG. 5. The coating 120 may comprise flexible materials such as acrylic, urethane, silicone, or similar materials.

Figure 6:
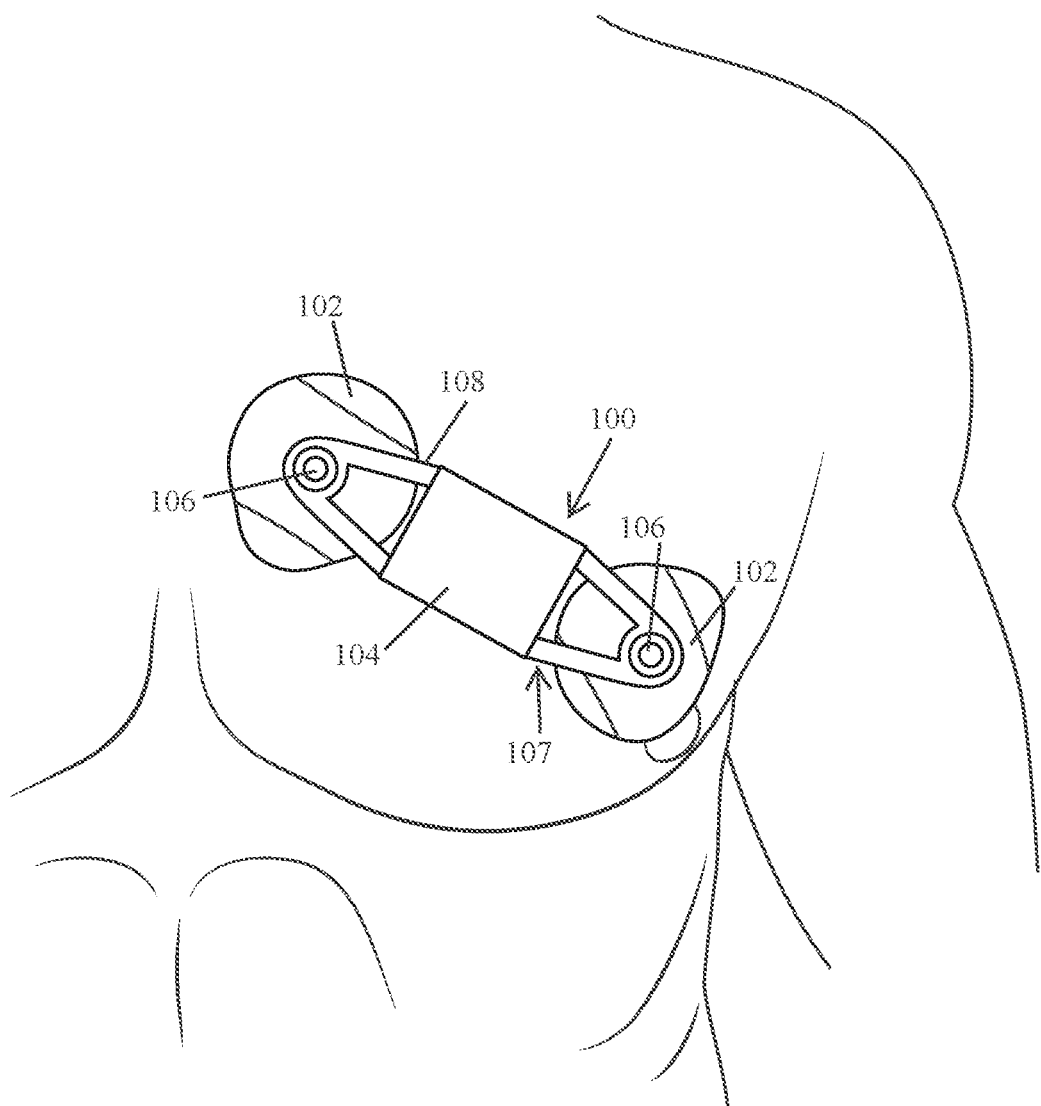
FIG. 6 depicts the device placed on the chest of a user.

In use, the patch 100 with electrodes 102 is attached to the body of a user. For example, as shown in FIG. 6, the patch 100 is attached to the chest of a user. In FIG. 6, the pulse oximeter 103, which is on the bottom surface of the central housing 104, is pressed into the body as a result of the mechanical spring mechanism 107. When the patch 100 is paired to an external device (ex: smart phone, tablet, etc.) over a radio protocol such as Bluetooth, the physiological data can be transmitted in real-time. FIG. 6 further shows the patch 100 with off-the-shelf electrodes 102, which can easily be attached and detached to the patch 100 through the electrode buckle snaps 106.

Figure 7:
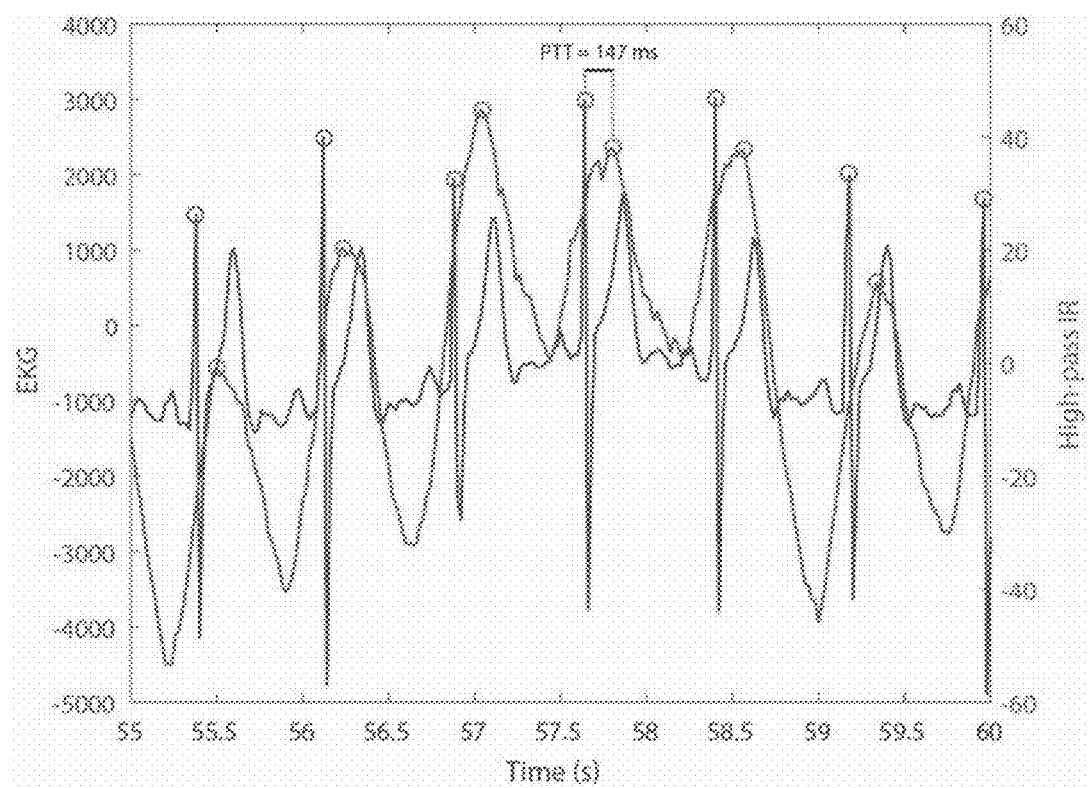
FIG. 7 is a graph showing data collected by the device, with pulse transit time identified.

A sample of collected EKG and PPG data can be seen in FIG. 7, and pulse transit time is highlighted. In this case, the raw EKG signal is plotted, along with a high-pass filter of the infrared PPG signal. A clear time-delay between the EKG and PPG peaks is seen, which is PTT, and in this case found to be approximately 147 ms. This value can then be calibrated to a user's blood pressure. For example, a user can perform calibration of the patch 100 using a traditional blood pressure cuff. Other data that can be used for calibration include the user's height, weight, gender, and age, which are characteristics that affect the relationship between PTT and blood pressure. In fact, given a large enough sample size of healthy volunteers who undergo this calibration, it is also possible for a user to obtain their blood pressure without the use of a traditional blood pressure cuff; rather, the user would enter their height, weight, gender, and age, and the calibration would be complete.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A wearable device capable of being affixed to a body of a user, the wearable device comprising:
    a base comprising a spring mechanism,
        wherein the base is adapted to be affixed to a planar surface of the body of the user;
    a pulse oximeter positioned on a bottom surface of the base,
        wherein the spring mechanism provides a bias force on the pulse oximeter to create a compressive force on the planar surface of the body of the user through the pulse oximeter,
        wherein the pulse oximeter does not penetrate the planar surface;
    a plurality of electrodes positioned on the bottom surface of the base,
        wherein the plurality of electrodes are separated by a distance providing different contact points for EKG measurements,
        wherein the pulse oximeter is positioned between at least two adjacent electrodes of the plurality of electrodes,
        wherein the plurality of electrodes are capable of acquiring EKG signals; and
    a printed circuit board attached to the base,
        wherein the printed circuit board electrically connects the pulse oximeter and the plurality of electrodes.

2. The device of claim 1, further comprising:
    a microprocessor,
        wherein the microprocessor receives PPG data from the pulse oximeter and EKG data from the plurality of electrodes.

3. The device of claim 2, further comprising:
    an EKG filter.

4. The device of claim 2, further comprising:
    an accelerometer.

5. The device of claim 1, wherein the base comprises a depressed center section with cantilevered arms extending from the depressed center section.

6. The device of claim 5,
    wherein the pulse oximeter is positioned in the depressed center section, and
    wherein the based comprises a stiff material capable of elastic deformation.

7. The device of claim 1, wherein the base comprises:
    a central housing;
    cantilevered arms extending from the central housing,
        wherein the cantilevered arms are flexible; and
    wires extending from the printed circuit board to the plurality of electrodes.

8. The device of claim 1, further comprising a plurality of electrode snaps attached to the base,
    wherein each of the plurality of electrodes connects to the plurality of electrode snaps.

9. The device of claim 1, wherein the base comprises a flexible material.

10. The device of claim 1, wherein the base has a non-planar shape.

11. The device of claim 1, wherein the spring mechanism is selected from the group consisting of: a curved cantilever beam, a helical-type spring, and a straight cantilever beam.

12. The device of claim 1, further comprising an insulating conformal coating affixed to the flexible printed circuit board.

13. The device of claim 1, further comprising:
    an adhesive disposed on a surface of the plurality of electrodes.

14. The device of claim 1, wherein the compressive force is perpendicular to the planar surface.

* * * * *